United States Patent [19]

Scott

[11] 4,015,465
[45] Apr. 5, 1977

[54] COLOR DISPLAYING FATIGUE SENSOR

[76] Inventor: William R. Scott, 532 Harbour Drive, Andalusia, Pa. 19020

[22] Filed: Mar. 31, 1975

[21] Appl. No.: 563,916

[52] U.S. Cl. .............................. 73/91; 116/114 AJ; 116/DIG. 34; 356/32
[51] Int. Cl.² .................. G01N 3/00; G01B 11/18
[58] Field of Search ... 116/114 D, 114 AJ, DIG. 34; 73/88 A, 91; 356/32, 34; 75/122

[56] References Cited

UNITED STATES PATENTS

| | | | |
|---|---|---|---|
| 2,816,236 | 12/1957 | Rosen | 356/32 X |
| 3,462,223 | 8/1969 | Tiemann et al. | 73/88 A |
| 3,715,915 | 2/1973 | Williams | 73/88 A |

*Primary Examiner*—Herbert Goldstein
*Assistant Examiner*—Daniel M. Yasich
*Attorney, Agent, or Firm*—R. S. Sciascia; Henry Hansen

[57] ABSTRACT

A method and apparatus for determining fatigue in a structural part. The fatigue sensor comprises, for example, a thin silver zinc film affixed to a structural member that is to be monitored for fatigue damage. Upon sufficient flexing or other cold working, the silver zinc film undergoes a color change, pink to silver, to thereby indicate that the structural member has reached predetermined fatigue levels.

5 Claims, 2 Drawing Figures

4,015,465

COLOR DISPLAYING FATIGUE SENSOR

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

This invention relates to fatigue sensors and in particular to fatigue sensors which indicate a predetermined level of fatigue by undergoing a color change.

The lifetime of a structural part such as an aircraft panel or bridge girder is governed to a large extent by the stresses and strains to which the part is subjected and the environmental conditions to which the part is exposed. High stresses, deleterious environmental conditions, or combinations of both, will adversely effect a structural part so that eventually failure of the part will result.

There exists much information about failure of structural parts. For example, there is a great deal of empirical information relating to the effect of stress and enviromental conditions on structural parts made from various materials of construction including various metals, nonmetals and composite materials. Also, it is known that in most instances fracture of a part will be initiated at the surface of the material. Further it is generally known that both maximum stresses and strains and environmental factors play a major role in contributing to failure of structural parts and that these factors interact in a way that is not completely understood. The exact stresses to which a structural part will be subjected and the exact environmental conditions which will be encountered are very seldom known with certainty. Thus, the empirical data which is available and the generalized concepts which are presently known are not generally sufficient to indicate the probable remaining lifetime of a structural part.

Consequently, designers are now forced to employ unduly conservative safety factors in the design of such structural parts thereby resulting in greatly increased costs, uncertainty, and the inability to take advantage of the full available strength of the materials employed.

To reduce the amount of uncertainty that pervades the art of fatigue measurement, fatigue gauges have been developed to provide some measurement of the overload and fatigue history of structural parts as well as the probable remaining lifetime of structural parts. However, presently employed fatigue gauges do not adequately satisfy these goals. They generally comprise plastic encased constantan metal foil which undergoes a resistivity change under cyclic flexing. When attached to a structural member the gauges give an indication in the form of a resistivity change of the integrated cyclic strain which the member experiences. These prior art gauges have several drawbacks: complicated fabrication procedures must be used to insure that the gauges have uniform resistivity; temperature changes produce significant changes in resistivity thus producing unacceptable inaccuracies in fatigue measurements; and to obtain even qualitative fatigue measurements, it is necessary to monitor such gauges with an external calibrated resistivity apparatus.

SUMMARY OF THE INVENTION

Accordingly, it is an object of this invention to provide a fatigue sensor which provides a measure of the overload and fatigue history of a structural part. A further object of this invention is to provide a fatigue sensor which when properly correlated with application experience gives an indication of the probable remaining lifetime of a structural part. It is a further object of this invention to provide a fatigue sensor which can easily be affixed to the external surface of a structural part and which provides a convenient visible indication of the irreversible changes of fatigue history of that structural part. It is a further object of this invention to provide a fatigue sensor which may be readily affixed to structural parts at points of high stress concentration. It is a further object of this invention to provide a fatigue sensor which is insensitive to usual ambient temperature fluctuations, which can be fabricated without elaborate and complicated techniques and which qualitatively signals a predetermined level of fatigue in a structural member by undergoing a visible color change. It is a further object of this invention to provide a fatigue sensor which undergoes a color change to thereby permit a quantitative measurement of fatigue when the sensor is viewed with appropriate optical instruments.

Briefly, these and other objects are achieved as follows. A thin film or foil of silver zinc is affixed to a thin flexible substrate and overlaid with a transparent protective coating. This composite structure, which comprises but one embodiment of the fatigue sensor of this invention, is affixed to a structural member by conventional means. As the structural member experiences cyclic loading, the silver zinc film is subjected to flexing, i.e. cold working. Upon suffering a predetermined level of cold working the silver zinc film undergoes a martensitic transformation which is accompanied by a color change, pink to silver. By visually observing the extent of the color change a qualitative indication of the amount of fatigue suffered by the structural member is obtained.

Other features and advantages of the invention will become apparent from the following detailed description when read in conjunction with the accompanying drawings.

DESCRIPTION OF THE PREFERRED EMBODIMENT

For convenience of expression, fatigue in a specimen, such as a structural member, is referred to as a form of cumulative material damage which results from the application of cyclic loading to the specimen. The extent of this damage increases with the number of cycles and the magnitude of the load applied to the specimen. Cyclic loading is defined as the application of a stress to the specimen which varies with time. (The period of time during which a load leaves equilibrium, reaches its maximum and minimum excursions and returns to equilibrium may be defined as one cycle.) Fatigue damage in materials is manifested by the hardening and embrittling of the material followed by the formation of cracks and ultimately by fracture.

Figure 1:
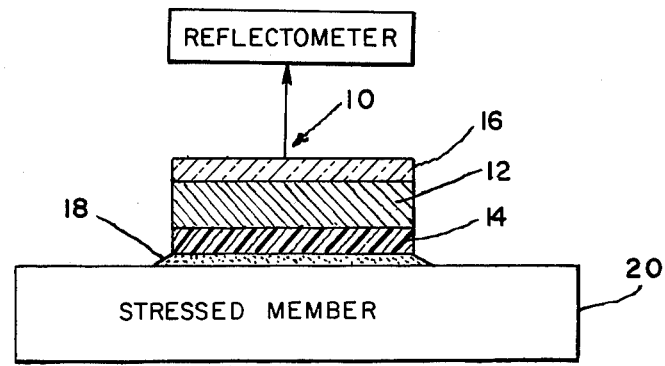
FIG. 1 is a schematic illustration of an embodiment of a fatigue sensor according to the invention.

Referring to FIG. 1, the fatigue sensor 10 of the present invention is shown in exaggerated form. The sensor 10 includes a silver zinc ($Ag_{54}Zn_{46}$) film having a thickness ranging from approximately 1,000 Angstroms to approximately one micron. In a preferred embodiment, the silver zinc film is conventionally vapor deposited or sputtered upon a flexible substrate 14 such as Mylar or polyimide. The substrate 14 preferably has a thickness of approximately one mil (0.001 inches). The silver zinc film 12 is overlaid with a transparent protective coating 16 which may be any suitable material such as clear epoxy. The transparent protective coating 16 and the flexible substrate 14 permit easy storage, handling and application of the silver zinc film 12 to a specimen 20. In the embodiment shown in FIG. 1, the sensor 10 is securely affixed to the specimen 20 by any suitable conventional means such as with a thin layer of conventional strain gauge cement 18. The specimen 20 may be any structural member which experiences stress and strain such as an aircarft panel or bridge girder.

After the sensor 10 is affixed to the specimen 20, it provides a visual indication of the presence of a predetermined level of fatigue in the specimen 20 in the following manner. As the specimen 20 experiences cyclic stresses, the silver zinc film 12 of the affixed sensor 10 undergoes a martensitic transformation upon sufficient flexing or other cold working being induced therein by the cyclic stresses experienced by, and the movements of, the specimen 20. Accompanying this martensitic transformation is a color change, pink to silver. By visually observing the extent of the color change, a qualitative indication of the amount of fatigue that the specimen 20 has suffered is obtained. The measurement of the amount of fatigue may be rendered quantitative by using a conventional reflectometer as shown in FIG. 1.

From the foregoing it is apparent that the silver zinc film 12 signals at least a predetermined threshold level of fatigue. The sensor 10 is thus singularly useful for indicating impending failure in a structural component for unlike presently used resistive fatigue sensors, the sensor 10 of the present invention allows a quick visual estimation of the cumulative effects of cyclic loading on the specimen 20 without the need for impedance meters and other cumbersome electrical equipment.

From the foregoing it is also apparent that the color change of the silver zinc film is an accurate indicator of the amount of cumulative fatigue damage that a specimen 20 has undergone.

Figure 2:
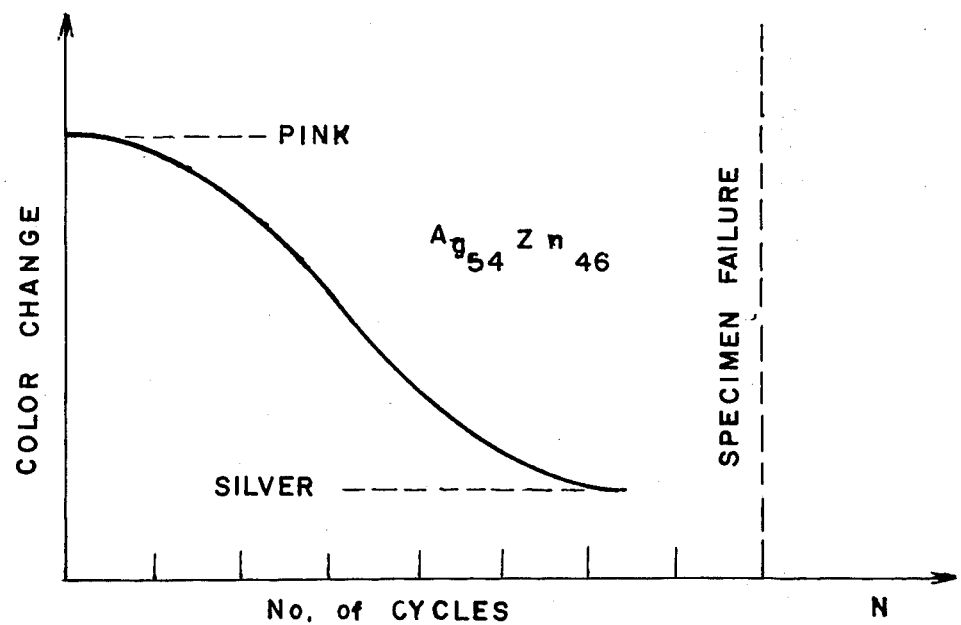
FIG. 2 is a graph of the color change experienced by a silver zinc film in response to a number of cycles of applied stress.

FIG. 2 indicates diagrammatically the expected color transition of the silver zinc film 12 from pink to silver as the specimen 20 to which it is attached is subjected to cyclic loading. The color damage is brought about by a martensitic phase transformation of the silver zinc film 12; the phase transformation depends upon the magnitude of the load applied to the specimen 20 and the number of loading cycles. In the absence of temperatures exceeding approximately 150° C., the phase transformation is believed to be irreversible for all practical purposes.

Instead of vapor depositing or sputtering the thin film 12 of silver zinc onto a flexible substrate 14, the silver zinc film 12 may be deposited directly onto the specimen with or without a transparent protective coating 16. Alternatively the silver zinc film 12 may be fabricated in the form of an annealed rolled foil which can be affixed to the specimen 20 with or without the flexible substrate 14 or the protective coating 16.

Other materials, such as CuAu or $Cu_3Au$, which undergo subtler color changes may be used in lieu of silver zinc; however these color changes can only be measured with a reflectometer for the color changes are too minute for visual detection. $Ag_{50}Zn_{50}$ may also be used with or without the addition of gold which increases phase stability. Another suitable alloy is zeta phase silver cadmium $Ag_{50}Cd_{50}$ which produces a visible color change, purple to pink, after experiencing relatively small amounts of cold working; both phases of the silver cadmium alloy are stable and the phase change is stable.

The material selected for the transparent protective coating 16 is not required to have extraordinary properties. As a minimum though, the coating 16 must not itself undergo a color change which would interfere with observation of the color change experienced by the metal alloy film 12.

Selection of an appropriate length, width and thickness for the metal alloy film 12 is not a critical process so long as enough of the metal alloy is used to allow the film 12 to be continuous and to exhibit bulk properties. On the other hand the film 12 cannot be made so large that it changes the properties of the specimen in the area where the sensor 10 is attached.

The specimen 20 to which the sensor 10 is affixed should be a ductile material such as steel, aluminum or brass and should not be a brittle material such as ceramic. In appropriate situations, conventional strain multipliers or strain reducers may be employed in conjunction with the fatigue sensor 10.

In sum, a novel fatigue sensor has been disclosed which is superior in operation because it relies only on the spectral reflectance of a silver zinc or other metal alloy film for proper operation. Hence, precision fabrication and high dimensional tolerances are not required in the manufacturing of the sensor 10. Because the color change of the silver zinc or silver cadmium film can be observed by the human eye, qualitative determinations of fatigue damage may be easily obtained. Equally as important, proper operation of the fatigue sensor is not altered by usual ambient temperature fluctuations.

Obviously many modifications and variations of the present invention are possible in the light of the above teachings. It is therefore to be understood that within the scope of the appended claims the invention may be practiced otherwise than as specifically described.

I claim:

1. A fatigue analysis process for determining the amount of fatigue experienced by a structural member subject to cyclic loading comprising:
   affixing a continuous metal alloy film to a portion of a surface of said specimen, said film being selected from the group consisting of $Ag_{50}Zn_{50}$, CuAu, $Cu_3Au$, $Ag_{54}Zn_{46}$ and $Ag_{50}Cd_{50}$, and having the property of undergoing a detectable color change upon experiencing sufficient cyclic stress; and
   observing said film to ascertain the extent of said color change.

2. A fatigue analysis process according to claim 1 further including the step of:
   detecting and quantitatively measuring said color change with a reflectometer.

3. A fatigue analysis process for determining the amount of fatigue experienced by a structural member subject to cyclic loading comprising:

affixing a continuous metal alloy film to a portion of a surface of said specimen, said film being selected from the group consisting of $Ag_{54}Zn_{46}$, $Ag_{50}Zn_{50}$ and $Ag_{50}Cd_{50}$, and having the property of undergoing a detectable color change upon experiencing sufficient cyclic stress; and observing said film to ascertain the extent of said color change.

4. A fatigue analysis process for determining the amount of fatigue experienced by a structural member subject to cyclic loading comprising:

affixing a continuous metal alloy film to a portion of a surface of said specimen, said film being selected from the group consisting of CuAu and $Cu_3Au$, and having the property of undergoing a detectable color change upon experiencing sufficient cyclic stress; and observing said film to ascertain the extent of said color change.

5. A fatigue analysis process according to claim 4 further including the step of:

detecting and quantitatively measuring said color change with a reflectometer.

* * * * *